(12) United States Patent
Shrout

(10) Patent No.: US 11,213,735 B2
(45) Date of Patent: Jan. 4, 2022

(54) EXERCISE APPARATUS

(71) Applicant: Jason Shrout, Eaton, OH (US)

(72) Inventor: Jason Shrout, Eaton, OH (US)

(73) Assignee: Jason Shrout, Eaton, OH (US)

( * ) Notice: Subject to any disclaimer, the term of this patent is extended or adjusted under 35 U.S.C. 154(b) by 362 days.

(21) Appl. No.: 16/362,421

(22) Filed: Mar. 22, 2019

(65) Prior Publication Data

US 2020/0298093 A1 Sep. 24, 2020

(51) Int. Cl.
*A63B 71/06* (2006.01)

(52) U.S. Cl.
CPC .... *A63B 71/0622* (2013.01); *A63B 2071/065* (2013.01)

(58) Field of Classification Search
None
See application file for complete search history.

(56) References Cited

U.S. PATENT DOCUMENTS

| | | | | |
|---|---|---|---|---|
| 6,066,105 A * | 5/2000 | Guillen | ............... | A61B 5/162 |
| | | | | 600/595 |
| 7,295,124 B2 * | 11/2007 | Guillen | ............... | A61B 5/162 |
| | | | | 434/236 |
| 2008/0249736 A1 * | 10/2008 | Prstojevich | ........ | A63B 24/0062 |
| | | | | 702/141 |
| 2009/0221337 A1 * | 9/2009 | Tranum | ............... | H04L 67/12 |
| | | | | 463/7 |
| 2012/0021872 A1 * | 1/2012 | Saha | ............... | A63B 69/0053 |
| | | | | 482/8 |
| 2013/0224708 A1 * | 8/2013 | Martin | ............... | A61B 5/6892 |
| | | | | 434/247 |
| 2015/0050629 A1 * | 2/2015 | Pease | ............... | A63B 43/00 |
| | | | | 434/247 |
| 2015/0099611 A1 * | 4/2015 | Lyman | ............... | A63B 71/14 |
| | | | | 482/83 |
| 2015/0306440 A1 * | 10/2015 | Bucher | ............ | A63B 21/00181 |
| | | | | 482/4 |
| 2017/0325518 A1 * | 11/2017 | Poupyrev | ............... | D02G 3/12 |
| 2017/0336172 A1 * | 11/2017 | Velez | ............... | F41G 3/2616 |

* cited by examiner

*Primary Examiner* — Justin S Lee

(74) *Attorney, Agent, or Firm* — Schwegman Lundberg & Woessner, P.A.

(57) ABSTRACT

Four striking panels having wireless sensors are arranged such that at least one striking panel is: in front of an athlete, behind the athlete, to the right of the athlete, and to the left of the athlete. A display is situated in front of the athlete. Randomly, a particular striking panel is presented on the display during an exercise routine. When the athlete strikes the appropriate corresponding panel based on detection of a wireless signal provided by the corresponding wireless sensor, a next randomly selected panel is presented on the display. This continues for a particular number of times or for a particular elapsed period of time. Response time metrics are retained for the routine and provided at the conclusion of routine.

10 Claims, 4 Drawing Sheets

EXERCISE APPARATUS

BACKGROUND

A number of sports require athletes to have quick hands and feet, such as basketball, football, soccer, tennis, lacrosse to name just a few. In addition, quick decision making is needed based on the location of the ball in these sports, such that muscle memory kicks in based on where the ball is located at any given moment during the game and a athlete's hands/feet respond accordingly.

There is a plethora of sports training aids and devices in the industry that attempt to assist in developing quickness and muscle memory in the athletes. Most training aids are non-interactive, meaning the athlete must perform some repetitive self-directed or predefined routine. Furthermore, the training aids are usually focused on one aspect of the athlete's performance and do not provide for improvement of multiple aspects.

Further, the more a training aid attempts to handle multiple aspects of the athlete's performance, the larger and more unwieldy the training devices become. This means that the devices are not portable nor compact, which restricts usage of the device to game fields or courts and which require larger transportation vehicles to transport the devices from location to location for use by the athletes. These more comprehensive devices also tend to be expensive and therefore unobtainable for many athletes.

Additionally, most training aids or devices are geared towards a single sport, such that these devices often provide little value to the athletes outside their designed sport.

SUMMARY

Various embodiments of the invention provide an apparatus, a method or using, and a system for exercising.

Specifically, and in one aspect, an exercise apparatus is provided. The apparatus includes: four posts arranged in a square or a rectangle; four sensors each sensor having a unique identifier and associated with a unique one of the posts; and a display. The display is situated outside the square or the rectangle and aligned with a center of the square or the rectangle on one side of the square or the rectangle. Moreover, the display is configured to: randomly present and identify a current sensor, change to a next randomly presented and identified sensor when the current sensor is touched by a user, and iterate for a predetermined amount of time or a predetermined number of presented sensors.

DETAILED DESCRIPTION

Figure 1:
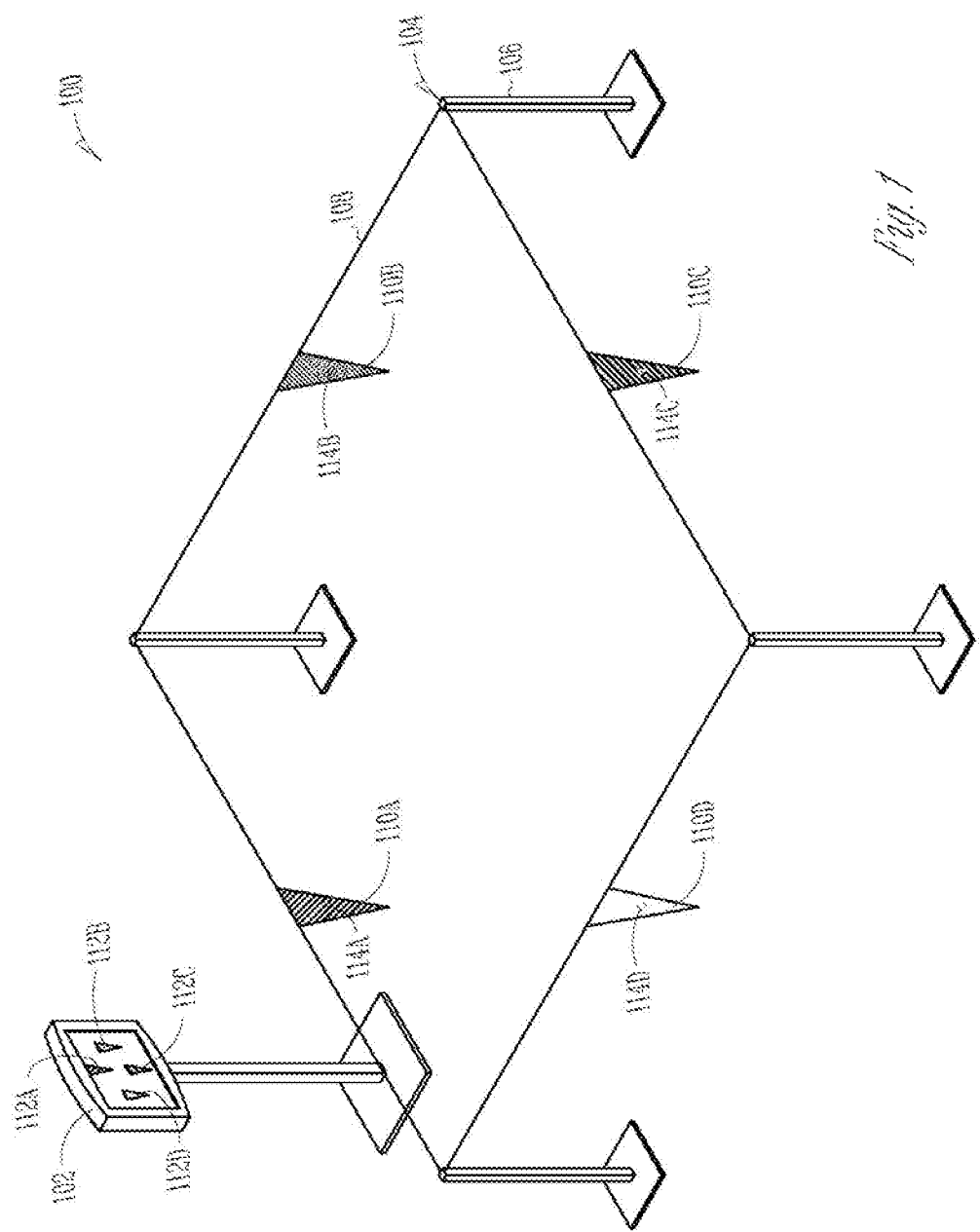
FIG. 1 is a diagram of an exercise apparatus, according to an example embodiment presented herein.

FIG. 1 is a diagram of an exercise apparatus 100, according to an example embodiment presented herein. The diagram is presented for purposes of illustration only and is not intended to limit embodiments of the invention to just the configuration detailed in the FIG. 1.

For example, many configurations of exercise apparatus's components with different dimensions and shapes can be used beyond what is illustrated in the FIG. 1, and any such configuration for the exercise apparatus 100 can be used with the teaching presented herein.

The apparatus 100 includes a control display 102, four posts 106, string/rope 108, and four flags 110A-110D. Each flag including a motion sensor 114A-114D.

The apparatus 100 provides a mechanism by which an athlete can train for improved foot quickness, decision making, and hand-eye coordination. The posts 106 are arranged as a court, the ropes 110A-110D are connected to the tops 104 of the posts 106 forming a ring or area that encloses the court or exercise area. In substantially the middle of each rope 106, the flag 110A-110D is affixed to its corresponding rope 106.

The control display 102 includes a processor, a display, memory, non-transitory computer-readable storage having executable instructions for the exercise routines, and at least one wireless transceiver. When the control display 102 is powered on wireless connections are established through the wireless transceiver to each of the motion sensors 114A-114D.

The athlete places himself/herself in the center of the configured court facing the display of the control display 102 and surrounded by the ropes/strings 108.

When an exercise routine is initiated on the control display 102, the executable instructions randomly select one of the four flags 110A-110D and waits for a wireless signal to be sent from the selected flag's motion sensor 114A-114D. To progress to a next randomly selected flag 1102A-110D, the athlete must move front to back and side to side and strike the corresponding flag 110A-110D that is presented on the display of the control display 102 by the executable instructions. As soon as the requested flag 110A-110D is touched (hit) by the hand of the athlete, the athlete is provided another different flag to strike (presented by the executable instructions on the display of the control display 102). An athlete cannot progress to a next flag 110A-110D for striking until the current flag 110A-110D illuminated on the display is touched by the athlete within the configured court. The transceiver of the control display 102 receives the wireless signal from the motion sensors 114A-114D as soon as the athlete causes the corresponding flag 110A-110D to move by striking the flag 110A-110D.

The executable instructions assign a unique identifier to each motion sensor 114A-114D, such that when the transceiver reports a wireless signal from a given motion sensor 114A-114D, the executable instructions can verify that the current requested flag 110A-110D was touched by the athlete. If a different flag 110A-110D was hit by the athlete than the current requested flag 110A-110D, then the executable instructions do not provide a next flag 110A-110D to the user via the display.

The executable instructions can be configured through the user-facing interface to continue to randomly select flags 110A-110D, one at a time, for a user-defined period of time (2 minutes, 5 minutes, etc.) or for a set amount flags (10 flags, 20 flags, etc.).

The executable instructions may also set a timer each time a new flag 110A-110D is requested and record an elapsed time from when the time was set until the corresponding flag's motion sensor 114A-114D reported its movement. The executable may maintain the total of these elapsed times on a per exercise routine to provide metrics to the athlete. For example, an athlete's total elapsed time for a given exercise routine along with a fastest response time may be maintained in the metrics. A total number of flags 110A-110D touched for a given exercise routine many also be maintained on a per routine basis. The executable instructions may also maintain dates with the metrics and retain the metrics for all exercise routines of the athlete, such that reports and graphs can be provided through the user-facing interface.

Furthermore, because each motion sensor 114A-114D includes a unique identifier, the executable instructions may be configured such that the athlete can identify the flag in front of the athlete, to the right of the athlete, to the left of the athlete, and behind the athlete at the start of a routine. This allows the executable instructions to maintain metrics for athlete response times going to the athlete's front, left, right, and back. Metrics and graphs may exposes weaknesses or strengths of the athlete for each direction and provide best response times for each direction.

In an embodiment, the control display 102 may include a Wi-Fi transceiver for connecting to the Internet or may use the wireless transceiver to connect to a mobile phone of the athlete. Here, the executable instructions allow the metrics to be reported to a cloud-based service, such that the reports can be viewed on a different device from the control display 102. The mobile phone includes a mobile application that interfaces to both the cloud service and the control display 102. In this way, the athlete can initiate an exercise routine or select an exercise routine from the mobile application and all metrics associated with an initiated exercise route and all previously completed exercise routines are available through the mobile application to the user. The control display 102 may also be remotely controlled through the mobile application.

In an embodiment, the cloud service maintains an account for a registered athlete, such that response metrics, total number of routines, best response times, best and worst directional response times, and custom reports are accessible via a web site and/or through a mobile application on the athlete's mobile phone. Different registered athletes can share their performance response times and custom-defined exercise routines with one another through the website. The website may also permit linking an athlete's social media account and provide automated posting of best performance metrics or routine completion to the athlete's social media account.

In an embodiment, the control display 102 and/or the mobile application may also link geographical data and weather data with each completed routine, such as longitudes, latitudes, altitudes, temperature. So, an athlete can obtain reports for weather conditions and physical locations that each routine was completed.

In an embodiment, the display of the control display 102 is a touchscreen.

In an embodiment, the flags 110A-110D are color coded (such as red, blue, green, yellow, etc.), when the executable instructions displays a randomly selected flag 110A-110D on the display of the control display 102, the flag 110A-110D is identified based on a particular color dot or symbol presented on the display.

In an embodiment, the executable instructions present a desired flag 110A-110D using an arrow that points up for forward, back for behind, right for the right, and left for the left. The arrows may be color coded or may not be color coded when presented on the display.

In an embodiment, the executable instructions present a symbol and/or a color in a particular location on the display, such as a top location for in front, bottom location for behind, a right location for the right, and a left location for the left.

In an embodiment, the sensors 114A-114D may be light based sensors that send a wireless signal to the control display 102 when a light beam is broken by the athlete's hand. So, the sensors 114A-114D can be motion based or light based or both.

In an embodiment, a mobile application can be used as the executable instructions to perform the processing discussed above for a given routine with the sensors 114A-114D on a tablet. In this embodiment, the tablet may be placed on a stand and the mobile application processed on the tablet as the control display 102. Here, a stand or post is used to affix and orient the tablet on the post to function as the control display 102.

The court comprises a user configured area inside the ropes/strings 108. The court can be custom configured in a square shape (such as shown in the FIG. 1) or a rectangle shape (as shown in the FIG. 2 with exercise apparatus 200). Furthermore, in an embodiment, the dimensions of the square (FIG. 1) or rectangle (FIG. 2) can be provided to the executable instructions to maintain with the performance metrics. For example, the center of the shape can be calculated by the executable instructions when provided through the user-facing interface by the user (e.g., 10 by 15 square foot rectangle). The distance from the calculated center to each flag can be maintained with the metrics, such that the athlete can evaluate his/her response times for specific distances.

Figure 2:
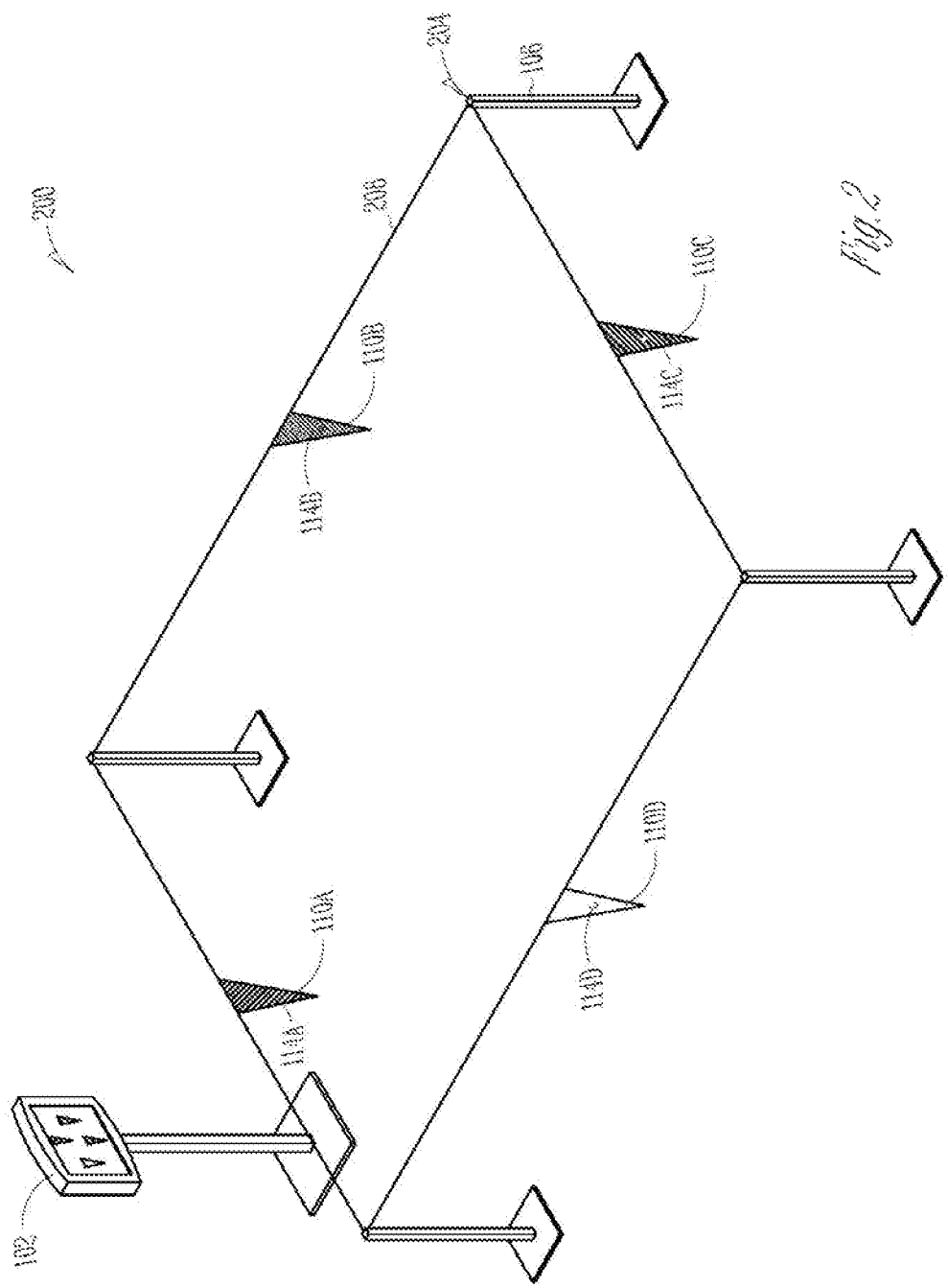
FIG. 2 is a diagram of another exercise apparatus, according to an example embodiment.

The FIG. 2 includes a rectangular shaped court having two ropes/strings 208 attached to the tops 204 of posts 106 that are longer than two remaining ropes/strings 208.

In an embodiment, the ropes/strings 108 and 208 are user adjustable, such that the athlete can determine the size and shape of the court by adjusting the lengths of each rope/string 108 and 208.

Figure 3:
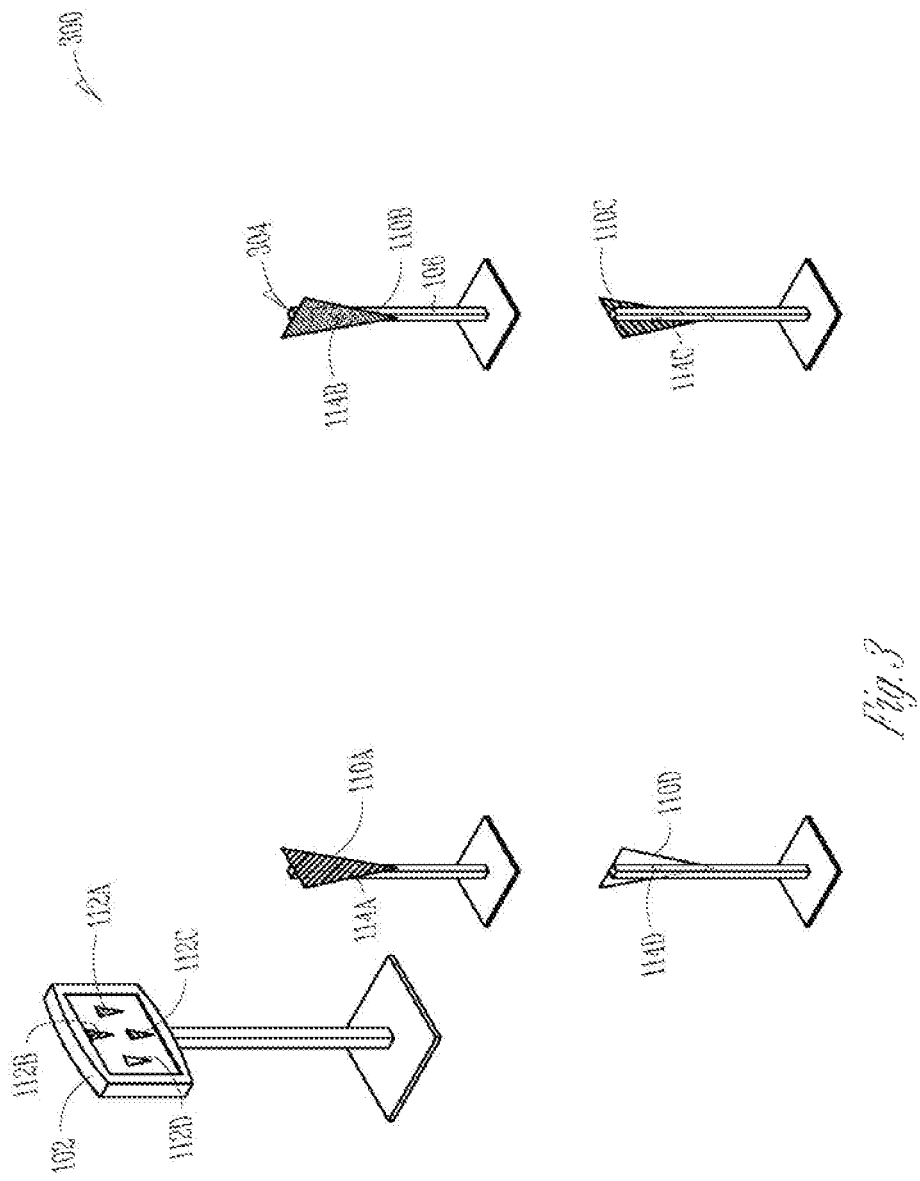
FIG. 3 is a diagram of a method yet another exercise apparatus, according to an example embodiment.

The FIG. 3 illustrates another exercise apparatus 300. In this configuration, apparatus 300 includes no ropes or strings, rather four posts 106 are provided and arranged in a shape by the athlete. Each post 106 includes a striking surface or flag 110A-110D and a motion and/or light wireless sensor 114A-114D. Each motion sensor 114A-114D is offset from a top 304 of each post 106.

The executable instructions process in the same manner as what was described above for the FIGS. 1 and 2 for apparatus 100 and 200, respectively. Here, there is no need for any suspension of a flag in centers of ropes as was discussed above with the FIGS. 2-3. The athlete uses his/her hand and strikes or touches the sensor 114A-114D when instructed to do so by the routine being processed by the executable instructions on the control display 102 (which may be a tablet device with a mobile application as discussed above with the FIGS. 1 and 2).

In an embodiment, the executable instructions presents a timer on the display representing an elapsed time that it takes the athlete to strike the appropriate panel/flag 110A-110D after being requested to strike that panel/flag 110A-110D. This is presented on the display along with the indication of the panel/flag 110A-110D and may be larger font than the flag/panel indications, such that during the routine, the athlete has real-time feedback on response performance.

In an embodiment, the control panel 102 includes a voice-based interface that allows the athlete to provide spoken instructions to the control panel during a routine, such as "pause," "stop," "start," etc. In an embodiment, the voice-based interface also permits the athlete to preconfigure a given routine or select a specific routine from a list of available routines, such as "the yellow panel is to my right," "the court is a 10 foot by 15 foot rectangle," "start a 5 minute routine," etc. In an embodiment, the voice-based interface permits the athlete to query for instance feedback on a given routine's performance metrics, such as "how did I do going behind me," "what was my slowest overall direction of movement," "what was my fastest response time," etc.

In an embodiment, the apparatuses 100, 200, and 300 may include just 2 sensors or three sensors in a custom layout defined by the athlete.

In an embodiment, the executable instructions permit one to two of 4 sensors to be excluded during a given exercise routine. This may be useful when the athlete is practicing going to just 2 to three directions instead of all 4 directions.

In an embodiment, the posts or poles 106 are approximately 3 foot in height; each post 106 includes a base into which a bottom end of the posts 106 can be snapped or screwed into. The posts 106 snap or screw into the bases at a center of the bases and a top end of the bases. The bases provide stability and allows the posts 106 to remain perpendicular to the ground/floor upon which the bases are placed. In an embodiment, the bases are hollow such that sand or water may be inserted into a hole with a cap of the base to provide weight and stability to each base.

In an embodiment, the control display 102 includes a post that is larger in height that the other 4 posts 106, such as 4 feet in height. The post for the control display 102 also snaps or screws into a base on its bottom end in the same manner that was described above for the court posts 106. The top of the post for the control display may screw or snap into a bezel or shell frame that holds the control display 102. In an embodiment, the bezel or shell frame is adjustable around the perimeter of the control display 102 to hold different sized control displays 102 (such as tablets of different sizes or dimensions).

In an embodiment, a post for the control display 102 is a same height or is substantially the same height as the 4 other posts 106.

In an embodiment, the bases and posts 106 are constructed of a sturdy plastic material.

In an embodiment, the bases, posts 106, control display post and base, ropes or strings 106, and flags (striking panels) 110A-110D with sensors 114A-114D are packaged together with a carrying bag for transport as apparatus 100, 200, and/or 300. The apparatuses 100, 200, and/or 300 are capable of being assembled as illustrated in the FIGS. 1-3 and disassembled and placed in the carrying bag. In an embodiment, the control display 102 is included with the apparatuses 100, 200, and/or 300 and the carrying bag. In an embodiment, the control display 102 is a tablet owned by the athlete where the tablet is configured with a mobile application representing the executable instructions discussed herein and above. The wireless communication with the tablet achieve via Bluetooth® transceiver that the mobile application utilizes to communicate with the sensors 114A-114D.

In an embodiment, the apparatuses 100, 200, and/or 300 include wired connections between the sensors 114A-114B to the control display 102, such that a transceiver is unnecessary and the signal received from each sensor 114A-114B is a wired signal. In an embodiment of this embodiment, the executable instructions of the control display 102 may be provided as firmware or specialized circuit that performs the processing discussed above for the exercise routine.

As used herein a "sensor" 114A-114B can be wired or wireless. The sensor 114A-114B that sends a signal over a wireless or wired connection to the control display 102. The sensor 114A-114B can be a wireless or wired button that when pressed provided the signal to the control display 102. Any wireless version of the sensor 114A-114B can be motion based and/or light based.

Figure 4:
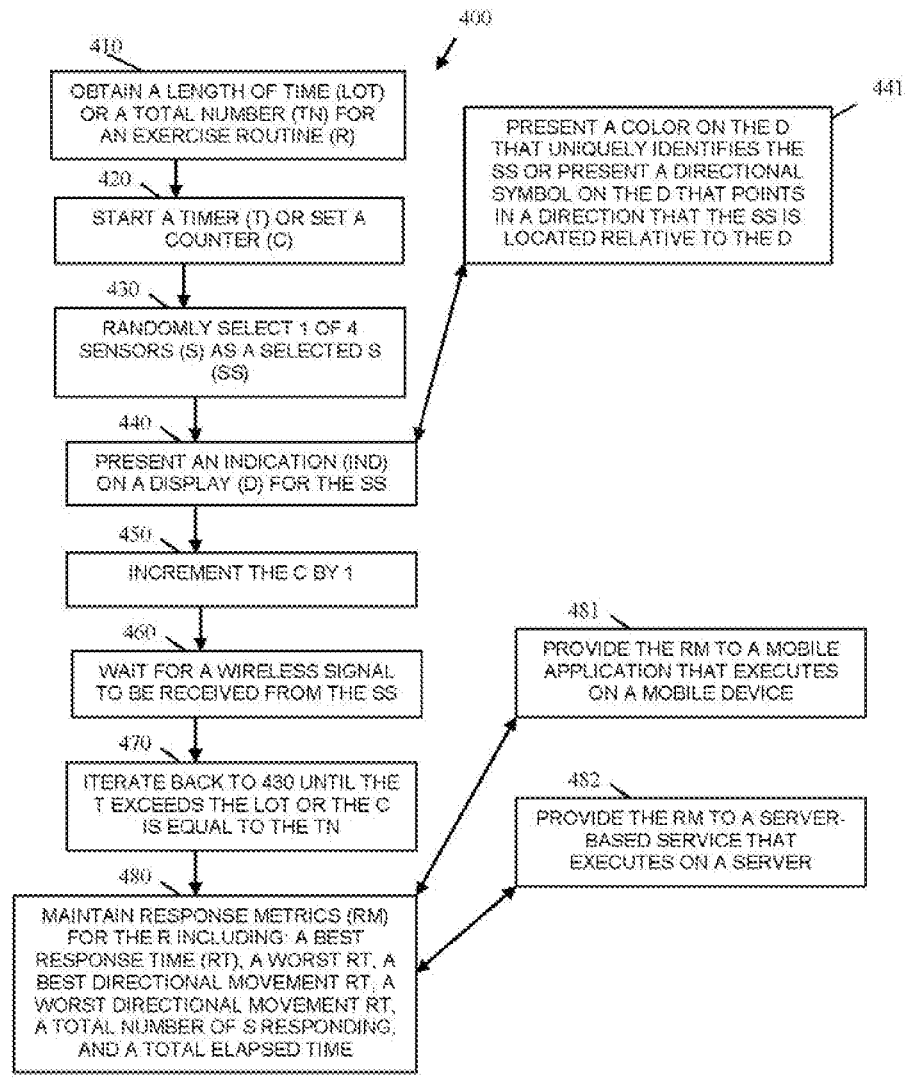
FIG. 4 is a diagram of method of operating an exercise apparatus, according to an example embodiment.

The FIG. 4 depicts a method 400 of operating the apparatuses 100, 200, and 300. The method 400 is implemented as executable instructions representing an exercise routine manager. The executable instructions are loaded from non-transitory storage into memory and executed by a hardware processor to perform the processing discussed herein. The exercise routine manager has access to one or more wireless connections during its operation.

In an embodiment, the device that executes the exercise routine manager is the control display 102.

In an embodiment, the device that executes the exercise routine manager is a tablet device.

The exercise routine manager processes with an athlete that has set up and is using the apparatus 100, 200, and/or 300.

In an embodiment, the exercise routine manager is the executable instructions discussed above with the apparatuses 100, 200, and 300.

At 410, the exercise routine manager obtains a length of time or a total number of sensors to touch for a given exercise routine. A user-facing interface allows the user/athlete to provide the length of time, the total number of sensors, and/or select a preset exercise routine from a list of saved exercise routines that include the length of time or the total number of sensors.

At 420, the exercise routine manager starts a time or sets a counter based on whether the exercise routine is associated with the length of time or the total number of sensors to touch during the exercise routine.

At 430, the exercise routine manager randomly selects 1 of 4 sensors as a selected sensor.

At 440, the exercise routine manager presents an indication on a display for the selected sensor.

In an embodiment, at 441, the exercise routine manager presents a color on the display that identifies the selected sensor or presents a directional symbol on the display that points in a direction that the selected sensor is located relative to the location of the display.

At 450, the exercise routine manager increments the counter by 1 after displaying each indication for the current selected sensor.

At 460, the exercise routine manager waits for a signal to be received from the selected sensor. That is, the exercise routine manager pauses until a signal is received from the selected sensor, which indicates that the user/athlete touched the sensor or touched a flag, button, or striking panel that includes the selected sensor. In an embodiment, the sensors are wireless sensors. In an embodiment, the sensors are wired sensors.

At 470, the exercise routine manager iterates back to 430 for a next randomly selected sensor until the timer exceeds the length of time or the counter is equal to the total number of sensors to touch for the exercise routine.

In an embodiment, at 480, the exercise routine manager maintains response metrics for the exercise routine. The response metrics include: a best response time, a worst response time, a best directional movement response time (e.g. to the athlete's right, left, front, back), a worst directional movement response time, a total number of sensors reporting for the exercise routine (e.g., total number of sensors touched or striking panel/flag having the sensors touched), and a total elapsed time for the exercise routine (e.g., from start to finish). As noted before, other metrics may be kept with an identifier associated with the exercise routine including, but not limited to, a date, a time, a current geographical location, a current altitude at the current geographical location, a current temperature, a current humidity, etc.

In an embodiment, the exercise routine manager provides a user-facing interface that allows custom reports and graphs to be generated based on the metrics for the exercise routine and other previously completed exercise routines.

In an embodiment, at 481, the exercise routine manager provides the response metrics to a mobile application that executes on a mobile device. In an embodiment, the mobile application provides a user-facing interface for obtaining reports and graphs based on the metrics. In an embodiment, the user-facing interface of the mobile application controls and configures the exercise routine manager.

In an embodiment, at 482, the exercise routine manager provides the response metrics to a server-based service that executes on a server (or a collection of servers logically cooperating as a cloud processing environment). In an embodiment, the server-based service includes a user-facing interface for obtaining reports and graphs based on the metrics.

In an embodiment, the mobile application described in 481 includes a service-based service interface for interacting with the server-based service described in 482.

In an embodiment of 481 and/or 482, a user-facing interface allows for posting of the response metrics and personal bests to a user/athlete's social media account for sharing with other users/athletes.

One now appreciates how an exercise apparatus and a method of using the exercise apparatus provides mechanism by which an athlete's foot quickness (footwork), hand-eye coordination, and decision making can be improved and tracked during an exercise routine for purposes of improving muscle memory performance in the athlete. The apparatuses (100, 200, and 300) and the routine can be used for performance enhancement in a variety of different sports, such as basketball, football, soccer, tennis, lacrosse, etc.

The above description is illustrative, and not restrictive. Many other embodiments will be apparent to those of skill in the art upon reviewing the above description. The scope of embodiments should therefore be determined with reference to the appended claims, along with the full scope of equivalents to which such claims are entitled.

The invention claimed is:

1. An apparatus, comprising:
sensors;
a display;
a processor;
non-transitory computer-readable storage medium having executable instructions;
the executable instructions when executed by the processor, cause the processor to:
randomly select a current one of the sensors;
present an indicator on the display for the current one of the sensors;
randomly select a next one of the sensors when a signal is received from the sensor associated with the current one of the sensors indicating that a touch was made proximate to the current one of the sensors;
iterate for a preconfigured amount of time or for a predefined number of randomly selected sensors;
a plurality of posts;
rope or string affixed to the tops of the posts to form a square court or a rectangle court; and
flags affixed to middles of ropes, each flag including one of the sensors.

2. The apparatus of claim 1, wherein the executable instructions when executed the processor further cause the processor to:
retain response time metrics that identity elapsed times between presenting the indicators and receiving the signals.

3. The apparatus of claim 1, wherein the executable instructions when executed by the processor further cause the processor to:
identify the preconfigured amount of time or the predefined number as a user selected exercise routine.

4. The apparatus of claim 1, wherein each flag is of a unique color.

5. The apparatus of claim 1, wherein the sensors include 4 sensors and the 4 sensors are wirelessly activated sensors that, communicate the signals over a wireless connection.

6. The apparatus of claim 1, wherein the sensors include 4 sensors and the 4 sensors are wired activated sensors that communicate the signals over a wired connection.

7. An apparatus, comprising:
four posts arranged in a square or a rectangle;
four sensors each sensor having a unique identifier and associated with a unique one of the posts;
four stings or ropes each string or each rope affixed to tops of two of the posts to define a perimeter of the square or the rectangle;
four flags, each flag affixed to a middle of each rope or each string, and each flag including a particular one of the four sensors; and
a display;
wherein the display is situated outside the square or the rectangle and aligned with a center of the square or the rectangle on one side of the square or the rectangle;
wherein the display configured to: randomly present and identify a current sensor, change to a next randomly presented and identified sensor when the current sensor is touched by a user, and iterate for a predetermined amount of time or a predetermined number of presented sensors.

8. The apparatus of claim 7 further comprising:
a display post adapted to hold the display outside of the square or the rectangle.

9. The apparatus of claim 8, wherein the display is a tablet that is affixed to the display post, the tablet executes instructions for randomly selecting and presenting indications for each of the sensors.

10. The apparatus of claim 7, wherein the display is further configured to provide response metrics that indicate response times between displaying particular sensors on the display and receiving responses from the particular sensors.

* * * * *

UNITED STATES PATENT AND TRADEMARK OFFICE
CERTIFICATE OF CORRECTION

| | |
|---|---|
| PATENT NO. | : 11,213,735 B2 |
| APPLICATION NO. | : 16/362421 |
| DATED | : January 4, 2022 |
| INVENTOR(S) | : Jason Shrout |

It is certified that error appears in the above-identified patent and that said Letters Patent is hereby corrected as shown below:

In the Claims

In Column 8, Line 11, in Claim 2, after "executed", insert --by--

In Column 8, Line 13, in Claim 2, delete "identity" and insert --identify-- therefor In Column 8, Line 25, in Claim 5, delete "that," and insert --that-- therefor In Column 8, Line 33, in Claim 7, after "ropes", insert --,--

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*